US012698311B2

(12) United States Patent
Devi et al.

(10) Patent No.: US 12,698,311 B2
(45) Date of Patent: Aug. 4, 2026

(54) PROCESS FOR THE PREPARATION OF AN ANTIMICROBIAL PEPTIDE

(71) Applicant: INSTITUTE OF BIORESOURCES AND SUSTAINABLE DEVELOPMENT, Imphal (IN)

(72) Inventors: Sarangthem Indira Devi, Imphal (IN); Ng Ngashangva, Imphal (IN); Pulok Kumar Mukherjee, Imphal (IN)

(73) Assignee: INSTITUTE OF BIORESOURCES AND SUSTAINABLE DEVELOPMENT (IN)

( * ) Notice: Subject to any disclaimer, the term of this patent is extended or adjusted under 35 U.S.C. 154(b) by 630 days.

(21) Appl. No.: 18/033,351

(22) PCT Filed: Dec. 6, 2021

(86) PCT No.: PCT/IB2021/061356
§ 371 (c)(1),
(2) Date: Apr. 23, 2023

(87) PCT Pub. No.: WO2022/084978
PCT Pub. Date: Apr. 28, 2022

(65) Prior Publication Data
US 2023/0416312 A1     Dec. 28, 2023

(30) Foreign Application Priority Data
Oct. 22, 2020     (IN) ............................. 202031046096

(51) Int. Cl.
| | |
|---|---|
| *C07K 14/195* | (2006.01) |
| *A01N 63/25* | (2020.01) |
| *C12N 1/20* | (2006.01) |
| *C12R 1/07* | (2006.01) |

(52) U.S. Cl.
CPC ............ *C07K 14/195* (2013.01); *A01N 63/25* (2020.01); *C12N 1/20* (2013.01); *C12R 2001/07* (2021.05)

(58) Field of Classification Search
CPC ...... C07K 14/195; A01N 63/25; A01N 37/46; C12N 1/20; C12R 2001/07; C12R 2001/01; A01P 1/00
See application file for complete search history.

(56) References Cited

U.S. PATENT DOCUMENTS

| | | |
|---|---|---|
| 9,809,865 B2 | 11/2017 | Teather et al. |
| 10,555,988 B2 | 2/2020 | Mysore Vishakante Gowda et al. |

FOREIGN PATENT DOCUMENTS

IN     201911008486 A     9/2020

OTHER PUBLICATIONS

Lee H.-G., Oh H.-M. Complete genome sequence of Paenibacillus Kribbensis producing RT bioflocculants. Submitted (Mar. 2017) to the EMBL/GenBank/DDBJ databases.*
Ngashangva et al. Antimicrobial Peptide From Endophyte, Frontiers in Microbiology, 2021, vol. 12, article656896, p. 1-12.*
Kim, J.F., et al., "Genome Sequence of the Polymyxin-Producing Plant-Probiotic Rhizobacterium Paenibacillus polymyxa E681," Journal of Bacteriology, vol. 192, Issue 22, pp. 6103-6104 (Nov. 2010).
Ngashangva, Ng., et al., "Screening of Endophytes from Traditionally Used Medicinal Plants of Manipur for Their Antimicrobial Activity: An Impact towards Future Drug Discovery," International Journal of Scientific Research in Biological Sciences, vol. 6, Issue 5, pp. 39-47 (Oct. 2019).

* cited by examiner

*Primary Examiner* — Jeanette M Lieb

(57) ABSTRACT

The present disclosure relates to a process for preparation of a peptide of sequence ID No. 1 having a formula $C_{231}H_{354}N_{66}O_{83}$ from an endophytic bacterium *Paenibacillus peoriae* IBSD35 isolated from the stem of *Millettia pachycarpa*. The genome size of *Paenibacillus peoriae* IBSD35 is 5.8 Mb, 45.6% GC content. The bioactive peptide designated as Peoriaerin IBSD35 of SEQ ID No. 1 was purified from the fermentation broth of *P. peoriae* strain IBSD35 and characterized with ESI (nano-spray)-TOF MS/MS spectrum. The peptide sequences were generated using MASCOT, MS-MS ion search. It has 54 amino acids residue and protein size is 5383.747 Da. The peptide of sequence ID No. 1 prepared by the present process exhibited broad spectrum of antibacterial and antifungal activity. It is highly resistant and stable to enzyme, detergent and environmental factors. It has the potential for drug development against AMR pathogens. It can also be used as food preservatives.

8 Claims, 5 Drawing Sheets
Specification includes a Sequence Listing.

PROCESS FOR THE PREPARATION OF AN ANTIMICROBIAL PEPTIDE

FIELD OF THE INVENTION

The present disclosure relates to a peptide with antimicrobial properties and a process of preparation thereof. More particularly, the present disclosure relates to a process for the preparation of an anti-microbial peptide (AMP) from *Paenibacillus peoriae* IBSD35, isolated from the stem of *Millettia pachycarpa*. The anti-microbial peptide prepared is having a strong and broad spectrum of action against antimicrobial resistant pathogens.

BACKGROUND OF THE INVENTION

The capacity of microbes to develop resistance is almost unlimited. Antimicrobial resistance (AMR) is the ability of a pathogenic microorganism to develop a resistance to the effects of an antimicrobial medication. AMR has become a very common and dangerous characteristic of pathogens and continuing to challenge the world medical sector. In response to increasing prevalence of antibiotic resistance in pathogens, there is an urgent need to explore the pharmacokinetic properties of many antimicrobial peptides produced by endophytes isolated from a variety of environments.

An endophyte is predominantly a bacterium or a fungus which exists in symbiotic relationship with the host plant. Endophytes are promising producers of a wide array of secondary metabolites with potential application in pharmaceuticals, healthcare and industries. Bacterial species belonging to the genus *Paenibacillus* produce antimicrobial compounds that are useful in medicine or as pesticides. *Paenibacillus peoriae* is an endophytic bacterium found in bark, stem and roots of the plants for example—*Millettia pachycarpa* Bentham and is known in the art for its anti-microbial properties due to the presence of anti-microbial peptides.

Antimicrobial peptides (AMPs) are evolutionary conserved and are produced by the innate immune system in all complex organisms. Polymyxins, are a class of AMPs, synthesized by a non-ribosomal process. Many species of *Paenibacillus* produce variants of polymyxins.

Numerous studies have been conducted to prepare AMPs or polymyxins. Shimizu et al., 1999 and Reddy et al., 2004 has developed a purified antibiotic peptide, Nisin, licensed for utilization as a food preservative by the US Food and Drug Administration (FDA). Pieren & Tigges 2012 demonstrated a naturally occurring means of combating pathogenic challenge by rapid microbicidal activity of AMPs. They exploit the bacterial cell membrane and, in many cases, they may have multiple targets within cells. Moreover, they are created from non-descript sequences of amino acids and less susceptible to resistant development.

Moreover, they resemble biosynthetic intermediates or endogenous metabolites and have shown potential and desirable therapeutic properties. Clay, 1989 disclosed clavicipitaceous endophytes of grasses having a huge potential as bio-control agents. They raise expectations of mutualism, functional significance, co-evolution, host-microbe interactions and plant microbiomes.

Samelis et al., 1994 have developed a bacteriocin known as Sakacin B produced by *Lactobacillus* sake isolated from Greek dry fermented sausages which form helix and shown strong antimicrobial activity. Stein et al., 2002 have developed two different lantibiotic-like peptides originating from the ericin gene cluster of *Bacillus subtilis* A1/3 that have strong antimicrobial activity against gram positive pathogens.

Mamsten, 2014 disclosed the important factors of AMPs for therapeutic applications are efficiency and selectivity while causing limited damage to the non-target cell. Giuliani et al., 2007 developed Melittin and Cecropin AMPs isolated from bee venom and hemolymph of moths respectively have shown to inhibit HIV-1 gene expression. Zasloff, 2002 disclosed that the defensins from insects are found to interfere with the development of *Plasmodium gallinaceum* oocytes, when injected into mosquitoes, and are highly toxic to its sporozoites. Human defensin peptides (HDPs) have shown their antimicrobial activity against a variety of pathogenic bacteria, including those that are resistant to conventional antibiotic.

Gautam et al., 2016 disclosed several linear amphiphilic peptides that are effective against different *Leishmania* stages, which will help, in designing novel drugs for the treatment of this tropical disease. Giuliani et al., 2007 disclosed antiviral activity of an AMP from Limulus *Polyphemus* by inhibiting the replication of enveloped viruses.

Ngashangva Ng et al., 2019 disclosed isolation of bioactive endophytes, *Paenibacillus* spp. from *Millettia pachycarpa* and AMPs from the former fermentation broth having strong and broad-spectrum of activity at a range of 1600 AU/ml.

U.S. Pat. No. 9,809,865 describes a *Paenibacillus* spp. isolate designated as *Paenibacillus polymyxa* JB05-01-1, as well as anti-microbial agent obtained from the bacterium or cell culture supernatant thereof.

IN288685 describes a peptide compound from *Bacillus clausii* with antimicrobial properties, to its preparation and to its applications. Indian Patent Application no. 2019110084 describes a process for the preparation of anti-microbial peptide from *Bacillus lichemformis*, isolated from pickles. The anti-microbial agents produced from probiotic bacteria are found to be useful for food preservation industry.

U.S. Pat. No. 10,555,988 describes anti-microbial peptide and variants thereof. The document discloses a method of killing or inhibiting growth of microbes with the disclosed peptide or variants thereof.

None of the prior art documents disclose a process for the preparation of anti-microbial peptide from *Paenibacillus peoriae* IBSD35 isolated from *Millettia pachycarpa*. The disclosed peptide exhibited both antibacterial and antifungal activity against AMR pathogens. It has shown strong and broad spectrum of antimicrobial activity against AMR/MDR pathogens viz. *C. albicans* ATCC 10231, *E. coli* ATCC 25922, *K. pneumoniae* ATCC 4352, *S. typhimurium* ATCC 14028, *C. tropicalis* ATCC 750 and *S. aureus* ATCC 25923) that has posed a major health concern worldwide. The disclosed process is advantageous as the novel peptide prepared is having a broad-spectrum action and strong antimicrobial activity against Gram-positive, Gram-negative and fungal AMR pathogens that makes it a potential candidate for drug development against AMR pathogens. Moreover, the anti-microbial peptide prepared by the process is a highly stable and non-toxic antimicrobial agent, thus having a potential as a food preservative other than the drug development.

The primary object of the present disclosure is to provide a process for the preparation of an AMP from *Paenibacillus peoriae* IBSD35 isolated from *Millettia pachycarpa*.

Another object of the present disclosure is to provide an anti-microbial peptide of SEQ ID No. 1 having a broad-spectrum action and strong antimicrobial activity against Gram-positive, Gram-negative and fungal AMR pathogens.

Yet another object of the present disclosure is to provide a process for the preparation of an anti-microbial peptide (Peoriaerin IBSD35) of SEQ ID No. 1 to counter AMR.

SUMMARY OF THE INVENTION

In an aspect of the present disclosure, there is provided a process for preparation of a peptide of sequence ID No. 1 having a formula $C_{231}H_{354}N_{66}O_{83}$, wherein the said process comprises the steps of:

(i) selecting plant *Millettia pachycarpa* harbouring microbial endophytes;

(ii) isolating endophyte *Paenibacillus peoriae* with surface sterilization technique;

(iii) culturing *Paenibacillus peoriae* on a growth medium at a temperature in the range of 35-40° C. for 5-7 days;

(iv) harvesting the cells by centrifugation for 10-20 minutes at a speed of 3000-4000 rpm and at a temperature of 4° C.;

(v) filtering the supernatant obtained in step (iv) through 0.2 μm ultrafiltration membrane to obtain a clarified supernatant;

(vi) subjecting the filtered supernatant obtained in step (v) with 70% ammonium sulphate precipitation and incubating for a period of 3-5 hours at room temperature;

(vii) centrifuging the mixture obtained in step (vi) at a speed of 4000 rpm for 30-40 minutes at a temperature of 4° C. to collect pellets, followed by dissolving the pellets in distilled water;

(viii) dialyzing the dissolved pellet mixture obtained in step (vii) against sodium phosphate buffer twice for a period of 12 hours;

(ix) purifying the solution obtained in step (viii) using column chromatography with DEAE-Cellulose and eluting with 100-700 mM NaCl followed by dialyses;

(x) analyzing the dialysate sample of step (ix) with RP-HPLC to obtain the antimicrobial peptide (AMP) peak;

(xi) analyzing the AMP peak with 12% Tricine SDS-PAGE and sequencing with LC-MS.

In an embodiment of the present disclosure, there is provided a process for preparation of a peptide of sequence ID No. 1 having a formula $C_{231}H_{354}N_{66}O_{83}$, wherein the isolated endophyte is *Paenibacillus peoriae* IBSD35.

In an embodiment of the present disclosure, there is provided a process for preparation of a peptide of sequence ID No. 1 having a formula $C_{231}H_{354}N_{66}O_{83}$, wherein the growth medium is selected from Luria Bertani and Brain Heart Infusion medium.

In an embodiment of the present disclosure, there is provided a process for preparation of a peptide of sequence ID No. 1 having a formula $C_{231}H_{354}N_{66}O_{83}$, wherein the peptide thus obtained is having a molecular weight of 5383.747 Dalton.

In an embodiment of the present disclosure, there is provided a process for preparation of a peptide of sequence ID No. 1 having a formula $C_{231}H_{354}N_{66}O_{83}$, wherein the peptide thus obtained forms alpha helices and is having at least 13 residues on the same hydrophobic surface.

In an embodiment of the present disclosure, there is provided a process for preparation of a peptide of sequence ID No. 1 having a formula $C_{231}H_{354}N_{66}O_{83}$, wherein the peptide compound thus obtained is thermostable at a temperature in the range of 20 to 121° C. and at a pH in the range of 4-9.

In an embodiment of the present disclosure, there is provided a process for preparation of a peptide of sequence ID No. 1 having a formula $C_{231}H_{354}N_{66}O_{83}$, wherein the peptide compound thus obtained is having strong and broad spectrum of antimicrobial activity against the gram positive, gram negative and fungal anti-microbial resistant pathogens selected from the group consisting of *Candida albicans* ATCC 10231, *Escherichia coli* ATCC 25922, *Klebsiella pneumoniae* ATCC 4352, *Salmonella typhimurium* ATCC 14028, *Candida tropicalis* ATCC 750 and *Staphylococcus aureus* ATCC 25923 and is useful as antimicrobial agent against animal, poultry feeds, food preservatives, plant pathogens and for therapeutic purposes.

In an embodiment of the present disclosure, there is provided a process for preparation of a peptide of sequence ID No. 1 having a formula $C_{231}H_{354}N_{66}O_{83}$, wherein the activity of peptide thus obtained is in the range of 1818.18 to 275862.06 AU/mg and is having a microbial inhibition count of 0.0365 μg $\mu l^{-1}$.

In a preferred embodiment of the present disclosure, there is provided a peptide of sequence ID No. 1, having a formula of $C_{231}H_{354}N_{66}O_{83}$, molecular weight 5383.747 Dalton and is 54 amino acids long with Glycine (G) as N-terminal residue, In a preferred embodiment of the present disclosure, there is provided a peptide of sequence ID No. 1, having the aliphatic index of 65.19 and is having GRAVY value of -0.224.

BRIEF DESCRIPTION OF THE ACCOMPANYING FIGURES

The following figures form part of the present specification and are included to further illustrate aspects of the present disclosure. The disclosure may be better understood by reference to the figures in combination with the detailed description of the specific embodiments presented herein.

Figure 4:
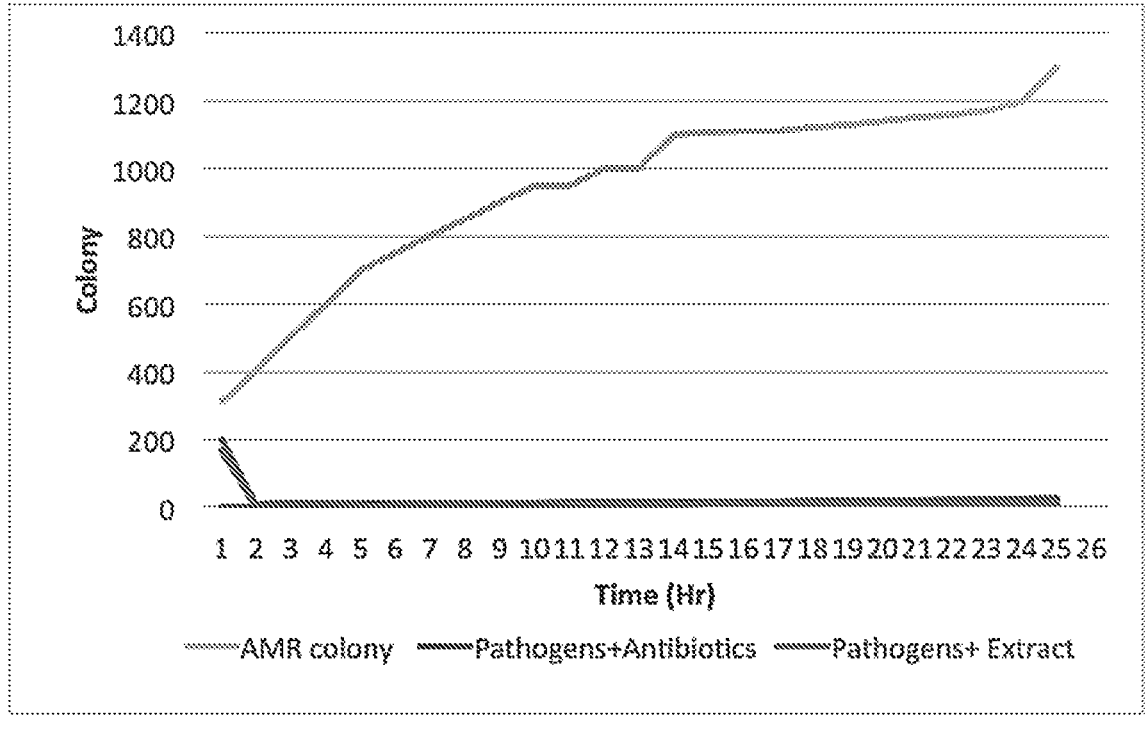

FIG. 4 depicts the Time-killing bioassay of crude extract against *S. aureus* ATCC 25923 at different time interval from 0-24 hours. (Yellow color indicates—pathogen without any agent; Red color indicates—pathogen with antibiotic; Blue color indicates—pathogens with antimicrobial agent).

Figure 5:
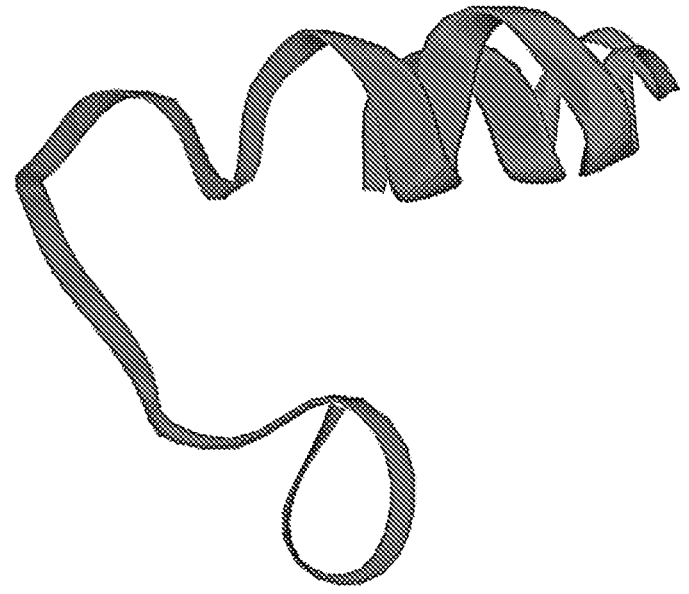

FIG. 5 depicts 3-D model of antimicrobial peptide of SEQ ID No. 1 isolated from *P. peoriae* IBSD35.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps of the process, features of the product, referred to or indicated in this specification, individually or collectively, and any and all combinations of any or more of such steps or features.

Definitions

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure is not to be limited in scope by the specific embodiments described herein, which are intended for the purposes of exemplification only. Functionally-equivalent products and methods are clearly within the scope of the disclosure, as described herein.

The present disclosure relates to a process for preparation of novel AMP designated as Peoriaerin IBSD35, from *Paenibacillus peoriae* IBSD35. It comprises the steps of (a) selection of plant, *Millettia pachycarpa*; (b) isolation of microbial endophytes with surface sterilization method and screening of its biological activity with spot-on-lawn antimicrobial bioassay using simple nutrients—Brain Heart Infusion and Luria Bertani media; (c) biochemical characterization of the bacterial endophytes as Gram-positive, rod-shaped, motile and spore-forming bacterial endophyte. The whole genome sequencing and analysis identified the endophyte as *P. peoriae* strain IBSD35, and it is an aerobic and nitrogen fixing bacterial endophyte. The genome size is calculated to be 3329.47 M bp with 45.79% GC content and harbored 25 SMs Biosynthetic gene cluster; (d) optimization of production media for secondary metabolites (SMs) production; (e) subjecting production media to partial purification by precipitated with 70% Solid ammonium sulphate; (f) subjecting the precipitate of step (e) for purification with DEAE ion exchanger resin for ion exchange column chromatography; (g) pooling the fraction eluted together, lyophilizing and dialyzing with 12400 Da MWCO; (h) The dialysate was run in semi-preparative RP-HPLC. The peaks of the RP-HPLC were pool together and electrophoresed (12% Tricine SDS-PAGE) with (49.5% T and 3% C) polyacrylamide gel at 30-60 V. The peaks retain the antimicrobial activity and its MIC was determined to be 0.0365 µg/µl; (i) AMP was sequence with LC/MS.

In an aspect of the present disclosure, there is provided a process for preparation of a peptide of sequence ID No. 1 having a formula $C_{231}H_{354}N_{66}O_{83}$, wherein the said process comprises the steps of:

(i) selecting plant *Millettia pachycarpa* harboring microbial endophytes;

(ii) isolating endophyte *Paenibacillus peoriae* with surface sterilization technique;

(iii) culturing *Paenibacillus peoriae* on a growth medium at a temperature in the range of 35-40° C. for 5-7 days;

(iv) harvesting the cells by centrifugation for 10-20 minutes at a speed of 3000-4000 rpm and at a temperature of 4° C.;

(v) filtering the supernatant obtained in step (iv) through 0.2 µm ultrafiltration membrane to obtain a clarified supernatant;

(vi) subjecting the filtered supernatant obtained in step (v) with 70% ammonium sulphate precipitation and incubating for a period of 3-5 hours at room temperature;

(vii) centrifuging the mixture obtained in step (vi) at a speed of 4000 rpm for 30-40 minutes at a temperature of 4° C. to collect pellets, followed by dissolving the pellets in distilled water;

(viii) dialyzing the dissolved pellet mixture obtained in step (vii) against sodium phosphate buffer twice for a period of 12 hours;

(ix) purifying the solution obtained in step (viii) using column chromatography with DEAE-Cellulose and eluting with 100-700 mM NaCl followed by dialyses;

(x) analyzing the dialysate sample of step (ix) with RP-HPLC to obtain the antimicrobial peptide (AMP) peak;

(xi) analyzing the AMP peak with 12% Tricine SDS-PAGE and sequencing with LC-MS.

In an embodiment of the present disclosure, there is provided a process for preparation of a peptide of sequence ID No. 1 having a formula $C_{231}H_{354}N_{66}O_{83}$, wherein the peptide compound is designated as Peoriaerin IBSD35. The details of purification scheme of the antimicrobial peptide Peoriaerin IBSD35 is mentioned in Table 1 below:

TABLE 1

| | | | | | | |
|---|---|---|---|---|---|---|
| | | Total | Total | Specific | | |
| | Vol | protein | activity | activity | Purification | Yield |
| Steps | (ml) | (mg) | (UA) | (UA/mg) | fold | (%) |

Purification scheme of the antimicrobial peptide.

| Steps | Vol (ml) | Total protein (mg) | Total activity (UA) | Specific activity (UA/mg) | Purification fold | Yield (%) |
|---|---|---|---|---|---|---|
| Crude | 2000 | 880 | 1,600,000 | 1818.18 | 1 | 100 |
| Supernatant | 2000 | 1,440 | 3,200,000 | 2222.22 | 1.22 | 200 |
| 70%(NH4)$_2$SO$_4$ precipitation | 30 | 14.40 | 48000 | 3333.33 | 1.83 | 3 |
| DEAE-C 700 mM Dialysis | 30 | 15 | 48000 | 3200 | 1.76 | 3 |
| RP-HPLC | 1 | 0.0029 | 800 | 275862.06 | 151.72 | 0.05 |

In an embodiment of the present disclosure, there is provided a process for preparation of a peptide of sequence ID No. 1 having a formula $C_{231}H_{354}N_{66}O_{83}$, wherein the growth medium is selected from Luria Bertani and Brain Heart Infusion medium.

In an embodiment of the present disclosure, there is provided a process for preparation of a peptide of sequence ID No. 1 having a formula $C_{231}H_{354}N_{66}O_{83}$, wherein culturing *Paenibacillus peoriae* IBSD35 on a growth medium at a temperature of 38° C. and pH-6.8.

The antimicrobial activity of the supernatant was quantitatively expressed as arbitrary unit. It is expressed as activity units (AU) per milliliter which is defined as the reciprocal of the highest dilution ($2^n$) that resulted in inhibition of *Staphylococcus aureus* ATCC 25923 as indicator lawn (Papagianni et al., 2006). It was calculated to be 1600 AU ml$^{-1}$.

The clear supernatant of the production media was partially purified by precipitated with 70% Solid ammonium sulphate. The precipitate was dissolved in distilled water and loaded with DEAE ion exchanger resin for ion exchange column chromatography. The fractions were eluted out with gradient NaCl (100-1M). The fraction eluted with 700 mM NaCl has shown the threshold absorbance at selected wavelengths of $\lambda_{205}$, $\lambda_{214}$, and $\lambda_{280}$. They were pooled together, lyophilized and dialyzed with 12400 Da MWCO and dialysis in semi-preparative RP-HPLC. The protein/peptide concentration and the retention of antimicrobial activity (FIG. 3) of the sample were estimated at each step of purification viz. cell debris pellet, supernatant, 70% ammonium sulphate precipitation, ion-exchange column chromatography and RP-HPLC purifications by UV-Vis spectrophotometry and Bradford assay. Its total activity, specific activity, purification fold and yield were calculated in relation to its initial activity (Table 1) above.

In an embodiment of the present disclosure, there is provided a process for preparation of a peptide of sequence ID No. 1 having a formula $C_{231}H_{354}N_{66}O_{83}$, wherein the peptide compound thus obtained is having a molecular weight of 5383.747 Dalton.

In an embodiment of the present disclosure, there is provided a process for preparation of a peptide of sequence ID No. 1 having a formula $C_{231}H_{354}N_{66}O_{83}$, wherein the peptide compound thus obtained forms alpha helices and is having at least 13 residues on the same hydrophobic surface.

The protein/peptide concentration and the retention of antimicrobial activity of the sample were estimated at each step of purification viz. cell debris pellet, supernatant, 70% ammonium sulphate precipitation, ion-exchange column chromatography and RP-HPLC purifications by UV-Vis spectrophotometry and Bradford assay.

In an embodiment of the present disclosure, there is provided a process for preparation of a peptide of sequence ID No. 1 having a formula $C_{231}H_{354}N_{66}O_{83}$, wherein the peptide compound thus obtained is thermostable at a temperature in the range of 20 to 121° C. and at a pH in the range of 4-9.

In an embodiment of the present disclosure, there is provided a process for preparation of a peptide of sequence ID No. 1 having a formula $C_{231}H_{354}N_{66}O_{83}$, wherein the peptide compound thus obtained is having strong and broad spectrum of antimicrobial activity against the gram positive, gram negative and fungal anti-microbial resistant pathogens selected from the group consisting of *Candida albicans* ATCC 10231, *Escherichia coli* ATCC 25922, *Klebsiella pneumoniae* ATCC 4352, *Salmonella typhimurium* ATCC 14028, *Candida tropicalis* ATCC 750 and *Staphylococcus aureus* ATCC 25923.

Figure 3:
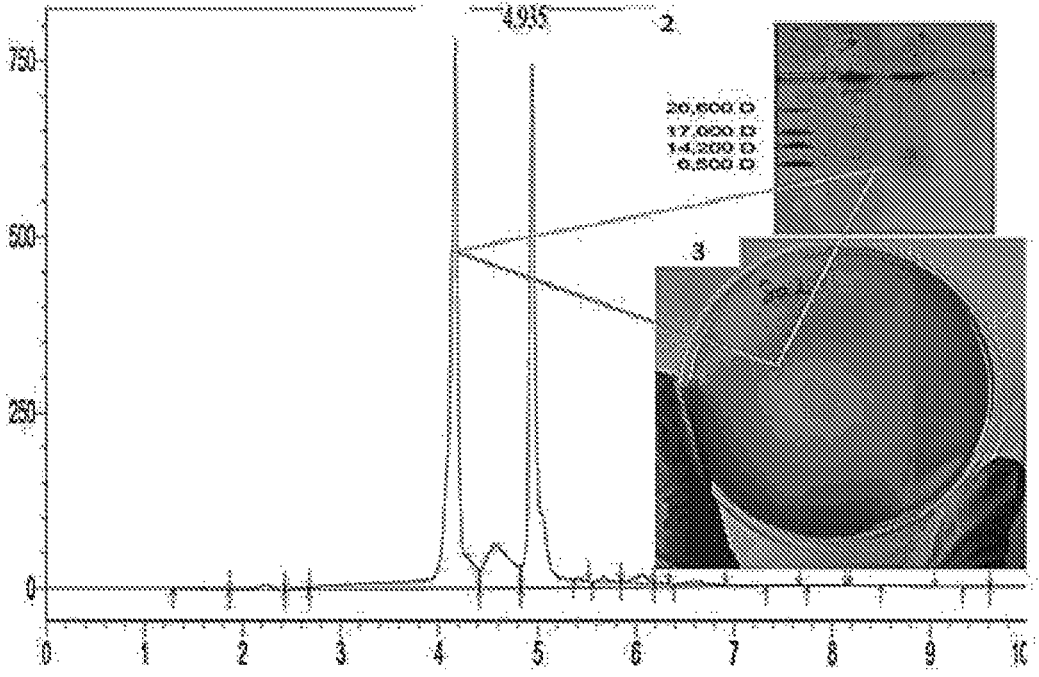
FIG. 3 depicts Gel overlay experiment. (1) Two peaks of RP-HPLC (2) Tricine SDS PAGE of the RP-HPLC Peak 1 (3) In-gel bioactivity assays of the RP-HPLC peak 1 against *S. aureus* ATCC 25923.

In an embodiment of the present disclosure, there is provided a process for preparation of a peptide of sequence ID No. 1 having a formula $C_{231}H_{354}N_{66}O_{83}$, wherein the Tricine SDS-PAGE In-gel overlay antimicrobial activity is tested against *S. aureus* ATCC 25923 (about 10$^6$ cells/ml) and checked for the halo zone of inhibition (FIG. 3)

In an embodiment of the present disclosure, there is provided a process for preparation of a peptide of sequence ID No. 1 having a formula $C_{231}H_{354}N_{66}O_{83}$, wherein the activity of peptide compound thus obtained is in the range of 1818.18 to 275862.06 AU/mg.

The peptides were recovered by lyophilization and stored at −20° C. until further use. The MIC of the RP-HPLC purified bioactive metabolite was determined to be 0.0365 μg μl$^{-1}$ with broth dilution bioassay. The two peaks were detected in the selected wavelengths of $\lambda$280 nm, $\lambda$205 nm and $\lambda$214 nm. However, only the peak 1 was selected for further study as it had shown more potency in antimicrobial susceptibility test.

In an embodiment of the present disclosure, there is provided a process for preparation of a peptide of sequence ID No. 1 having a formula $C_{231}H_{354}N_{66}O_{83}$, wherein microbial inhibition count of peptide compound thus obtained is 0.0365 μg μl$^{-1}$.

In an embodiment of the present disclosure, there is provided a process for preparation of a peptide of sequence ID No. 1 having a formula $C_{231}H_{354}N_{66}O_{83}$, wherein purification on fold of peptide compound thus obtained is 151.72 starting from the initial supernatant.

The amino acid sequence of the AMP was generated with LC/MS and its primary characters and 3-D model was determined using proteomics analysis tools. It forms helix and it's 3-D model was generated using SWISS-MODEL and deposited on Model archive with accession number as ma-1ea5d.

In an embodiment of the present disclosure, the antimicrobial peptide Peoriaerin IBSD35 prepared by the process is having 54 amino acids residues and its protein size or residue of the peptide is 5383.747 Da.

In an embodiment of the present disclosure, the antimicrobial peptide Peoriaerin IBSD35 prepared by the process is having a total net charge is −3.

In an embodiment of the present disclosure, the atomic formula of the antimicrobial peptide Peoriaerin IBSD35 prepared by the process is $C_{231}H_{354}N_{66}O_{83}$. The N-terminal of the sequence considered is Glycine (G).

Primary structure analysis of peptide shows the amino acid composition of peptide. In an embodiment of the present disclosure, the pH of the antimicrobial peptide Peoriaerin IBSD35 prepared by the process is 4.23 which indicated its acidic nature. The instability index (II) of the peptide Peoriaerin IBSD35 prepared by the process is computed to be −1.98. This classifies the Peoriaerin IBSD35 prepared by the process as stable. Further, the aliphatic index and GRAVY of the Peoriaerin IBSD35 prepared by the process is calculated as 65.19 and −0.224 respectively.

Although the subject matter has been described in considerable detail with reference to certain preferred embodiments thereof, other embodiments are possible.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods, the exemplary methods, devices and materials are described herein. It is to be understood that this disclosure is not limited to particular methods, and experimental conditions described, as such methods and conditions may vary.

Example 1

Sample Collection and isolation of endophytes: Plants were collected from Ukhrul (N025°07.953' and E094°16.594'), Manipur which lies in the Indo-Burma Biodiversity Hot Spot Region (Tattersfield et al., 1940; Costello & Butler, 1948; Myers et al., 2000). The plants stems were thoroughly rinsed on running tap water to remove soil and organic debris and then washed with Tween 20. Subsequently, the sample (2 inches) were sequentially treated with chemicals to kill all surface microbes (Clay, 1990; Petrini, 1984), and then aseptically dissected into pieces (1-2 cm).

The samples pieces were inoculated on Luria Bertania (LB) agar plates and incubated at 25° C. concurrent with the climatic condition of the plants sample habitat (Schulz & Boyle, 2005). The controlled aseptic sterilization was performed by spreading residue of the final washing distilled $H_2O$ (200 µl) on LB agar and potato dextrose agar (PDA) plates (Schulz et al., 1997). The contamination was further checked by rolling the sample on the agar lawn and incubated at room temperature for 3 days.

Morphology and molecular characters of the endophyte: The endophytes were observed with the microscopes (Strobel et al., 1964) and the morphological and cultural characteristics of the bioactive bacterial strain were examined by following the keys of Bergey's manual of determinative bacteriology (Ash et al., 1993; Holt et al., 1994). The phenotypic characters were determined with Gram staining (Breed et al., 1957; Brock, 1999). The strain motility was tested by hanging drop method and observed on concave glass slide with Phase contrast microscope (Zeiss, Imager. Z2) (Brock, 1999). The crude genomic Deoxyribonucleic acid (DNA) was extracted with Cetyl Trimethyl Ammonium Bromide (CTAB) method and the molecular characterization was performed by whole genome sequencing (WGS) (Illumina HiSeq 2500) (Wilson, 1997; Ma et al., 2011; Jeong et al., 2011).

Example 2

Figure 1:
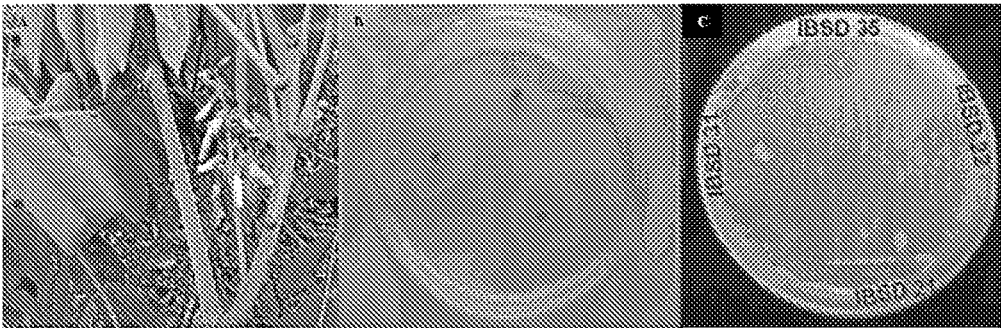
FIG. 1 depicts (A) The plant, *Millettia pachycarpa* Bentham (B) Inoculation of pieces of plant stem on agar plate (C) Spot-on-lawn bioassay of bacterial endophyte on pathogen (*Staphylococcus aureus* ATCC 259233) lawn showing a clear zone of antimicrobial activity.

Antibacterial Activity Test: In order to determine the antibacterial activity of purified peptide, antibacterial activity test was performed using Spot-on-lawn antimicrobial bioassay in which a single pure isolate was spotted on MHA (20 ml) lawn (w/v 1% agar) seeded with test strains (50 µl) of 0.5 Macfarland standard (1.5×108 cfu/ml). The plates were incubated at 37° C. overnight as per the test pathogens favorable condition (FIG. 1). An Antibacterial Activity (AA) on test pathogen lawn was measured using antimicrobial susceptibility Scale in millimeter with 6 mm as a threshold of positive.

Figure 2:
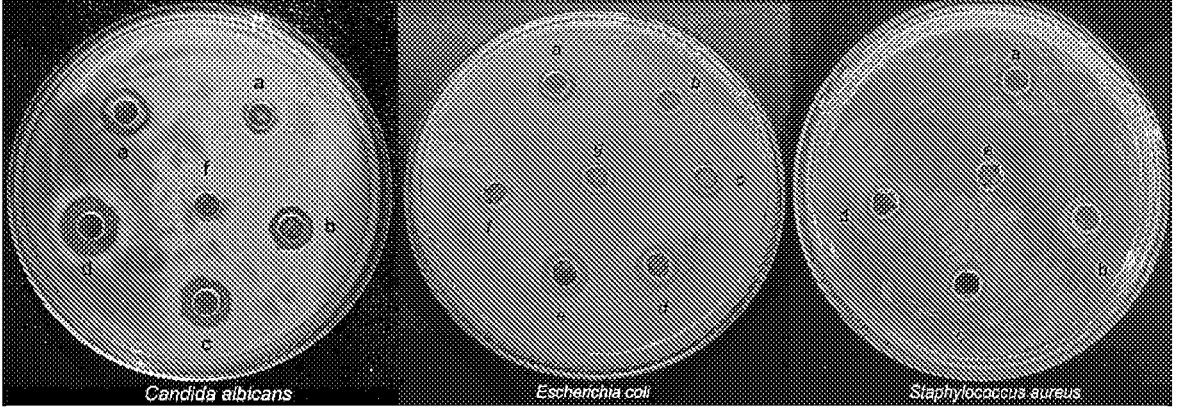
FIG. 2 depicts the Cut well agar diffusion bioassay of antimicrobial agent against representative pathogen (A) *C. albicans* ATCC 10231, (B) *E. Coli* ATCC 25922, and (C) *S. aureus* ATCC 25923 (a) crude (b) supernatant (c) ammonium sulphate precipitate (d) 700 mM DEAE ion exchange chromatography (e) Dialysis (f) $H_2O$ control.

Spectrum of antimicrobial activity: The spectrum of activity was determined from the selected test pathogens viz. *S. aureus* ATCC25923, *C. ablicans* ATCC 10231, and *E. coli* ATCC 25922 which represented as a Gram (+), Gram (−) and fungal pathogens (FIG. 2). The bacterial strain IBSD35 (NCBI accession no. NZ_PTJM01000000) which exhibited strong and broad spectrum of AA LB broth were harvested. The cell debris were removed by centrifugation at 4000 rpm for 15 min at 4° C. The supernatant was harvested for antimicrobial bioassay and preserved at 4° C. for further purification (Fujita et al., 2007). The well loaded with samples that shown a clear halo zone of inhibition (at least 6-7 mm diameter) were taken as positive against the selected Gram (+ve), Gram (−ve) and fungal pathogens. The bacterial endophytic strain IBSD35 isolated from *M. pachycarpa* has shown a broad-spectrum of AA against the representative test pathogens in the preliminary Spot-on-lawn bioassay and the Cut-well agar diffusion bioassay (FIG. 2). It inferred antifungal, antibacterial and antimicrobial property of the endophyte strain IBSD35.

Example 3

Antifungal test: In order to determine the antifungal activity of purified peptide, antifungal test was performed using Agar-well diffusion bioassay in which the partially purified supernatant was loaded on wells of MHA (20 ml) lawn (w/v 1% agar) seeded with test strains (*C. ablicans* ATCC 10231) (50 µl) of 0.5 Macfarland standard (1.5×10^8 cfu/ml). The plates were incubated at 30° C. overnight as per the test pathogens favorable condition. An Antifungal activity on test pathogen lawn was measured using antimicrobial susceptibility Scale in millimeter with 6 mm as a threshold for positive. It has shown strong antifungal activity at the range of 12 mm as measured with antimicrobial susceptibility scale (FIG. 2). Moreover, it has shown antifungal activity against *Candida tropicalis* ATCC 750.

Example 4

Time-kill bioassay: The time-kill study was performed with the selected test pathogen to further define the antibacterial activity of the crude extract. Moreover, it allows assessing the rate of bactericidal activity at varying antimicrobial agent concentrations over time. The time-killing curve study was performed in duplicate using concentrations or dose of 0.5, 1, 1.5, 2, 2.5, 3, 3.5, and 4×MIC of crude extract for 24 hours of incubation. The activity was observed at every hour and plated on the MHA agar to count the colony.

The test strains, *S. aureus* ATCC 25923 was grown as described before. To minimize the effect of antibiotic carryover, the samples were centrifuged (15000 rpm, 5 min, 4° C.) before plating out and the antibiotic medium was replaced with fresh BHI broth. The positive control is without antimicrobial agent and the negative control is without test microorganisms but with antimicrobial agents.

The antimicrobial action was observed after 2 hours of incubation. SEM imaging indicated that the pathogen colony are slowly disappearing which correlated with the decreased colony count on time-killing bioassay plating (FIG. 4). The slower kinetics of killing suggested that antimicrobial peptide might be penetrating the cell membrane and transport inside the cell cytoplasm to cause the effect. The leakage of DNA and proteins were not observed. So, the antimicrobial or bacteriocin must be a pore former. However, the present AMP has broad spectrum of activity which in fact most pore former AMPs are supposed to have narrow spectrum of activity and generally closely related species. The absorbance at wavelength of $\lambda260$ and $\lambda280$ were measured with UV spectrometry. The OD at $\lambda600$ nm was 1.409 and there is no any evident of DNA and protein leakage in the test broth. It showed that the cell might be killed by penetrating inside the cell cytoplasm and cell periplasm.

Example 5

Effect of Temperature and Inorganic Solvents:

The AMP, Peoriaerin IBSD35 is a very stable biomolecule and works on a wide range of temperature and pH and withstand against inorganic solvents as shown in Table 2 below.

TABLE 2

Retention of antimicrobial activity after treatment with inorganic solvents and temperature, (+) retention, (−) loss.

| Treatment | Zone of inhibition diameter (mm) | Activity |
|---|---|---|
| Inorganic solvents (1:1) | | Activity |
| Methanol | 9 | + |
| Butanol | 10 | + |
| Ethyl acetate | 12 | + |
| Petroleum ether | 8 | + |
| Isopropanol | 8 | + |
| Acetone | 12 | + |
| Temperature (° C.) | | Activity |
| 20 | 11 | + |

TABLE 2-continued

Retention of antimicrobial activity after treatment with inorganic solvents and temperature, (+) retention, (−) loss.

| Treatment | Zone of inhibition diameter (mm) | Activity |
|---|---|---|
| 40 | 10 | + |
| 60 | 10 | + |
| 80 | 11 | + |
| 100 | 10 | + |
| 121 | 14 | + |

Example 6

Effect of Physiological Enzymes:

The purified AMP, Peoriaerin IBSD35 is treated with proteolytic enzymes, it can withstand against enzymes and its antimicrobial activity was checked by measuring the zone of inhibition as shown in Table 3 below.

TABLE 3

Retention of antimicrobial activity after treatment with degradative enzymes, (+) retention, (−) loss.

| Treatment | Zone of inhibition diameter (mm) | Activity |
|---|---|---|
| Proteinase K (1 mg/ml) | 11 | + |
| Catalase | 10 | + |
| Pectinase | 9 | + |
| Cellulase | 9 | + |
| Pepsin | 10 | + |

Example 7

Effect of Surfactants:

The surfactants such as sodium dodecyl sulphate (SDS), Tween 20, Tween 80 and Triton X were incubated with the anti-microbial compound, Peoriaerin IBSD35. The AMP works and does not inactivate in the presence of surfactants as shown in Table 4 below.

TABLE 4

Retention of antimicrobial activity after treatment with detergents, (+) retention, (−) loss.

| Treatment | Zone of inhibition diameter (mm) | Activity |
|---|---|---|
| Detergents (1:1) | | Activity |
| SDS | 14 | + |
| Triton X | 14 | + |
| Tween 20 | 13 | + |
| Tween 80 | 12 | + |
| Control | − | − |

The invention claimed is:

1. A process for preparation of a peptide of sequence ID No. 1 having a formula $C_{231}H_{354}N_{66}O_{83}$, wherein the process comprises the steps of:

(i) selecting plant *Millettia pachycarpa* harboring microbial endophytes;

(ii) isolating endophyte *Paenibacillus peoriae* with surface sterilization technique;

(iii) culturing *Paenibacillus peoriae* on a growth medium at a temperature in a range of 35-40° C. for 5-7 days to obtain cells;

(iv) harvesting the cells by centrifugation for 10-20 minutes at a speed of 3000-4000 rpm and at a temperature of 4° € 4° C. and obtaining a supernatant;

(v) filtering the supernatant through a 0.2 μm ultrafiltration membrane to obtain a clarified supernatant;

(vi) subjecting the clarified supernatant obtained in step (v) with 70% ammonium sulphate precipitation and incubating for a period of 3-5 hours at room temperature to obtain a mixture;

(vii) centrifuging the mixture obtained in step (vi) at a speed of 4000 rpm for 30-40 minutes at a temperature of 4° C. to collect pellets, followed by dissolving the pellets in distilled water;

(viii) dialyzing the dissolved pellets obtained in step (vii) against sodium phosphate buffer twice for a period of 12 hours to obtain a solution;

(ix) purifying the solution obtained in step (viii) using column chromatography with DEAE-Cellulose and eluting with 100-700 mM NaCl followed by dialyses to obtain a dialysate sample;

(x) analyzing the dialysate sample of step (ix) with RP-HPLC to obtain an antimicrobial peptide (AMP) peak; and (xi) analyzing the AMP peak with 12% Tricine SDS-PAGE and sequencing with LC-MS.

2. The process as claimed in claim 1, wherein the isolated endophyte is *Paenibacillus peoriae* IBSD35.

3. The process as claimed in claim 1, wherein the growth medium is Luria Bertani, or Brain Heart Infusion medium.

4. The process as claimed in claim 1, wherein the antimicrobial peptide has a molecular weight of 5383.747 Dalton.

5. The process as claimed in claim 1, wherein the antimicrobial peptide forms alpha helices and has at least 13 residues on a hydrophobic surface.

6. The process as claimed in claim 1, wherein the antimicrobial peptide is thermostable at a temperature in a range of 20 to 121° C. and at a pH in a range of 4-9.

7. The process as claimed in claim 1, wherein the antimicrobial peptide has a strong and broad spectrum of antimicrobial activity against the gram positive, gram negative and fungal anti-microbial resistant pathogens selected from the group consisting of *Candida albicans* ATCC 10231, *Escherichia coli* ATCC 25922, *Klebsiella pneumoniae* ATCC 4352, *Salmonella typhimurium* ATCC 14028, *Candida tropicalis* ATCC 750, and *Staphylococcus aureus* ATCC 25923 and acts as an antimicrobial agent against animal, poultry feeds, food preservatives, plant pathogens and for therapeutic purposes.

8. The process as claimed in claim 1, wherein the activity of antimicrobial peptide is in a range of 1818.18 to 275862.06 AU/mg and has a microbial inhibition count of 0.0365 μg μl−1.

* * * * *

SEQUENCE LISTING

<160> NUMBER OF SEQ ID NOS: 1

<210> SEQ ID NO 1
<211> LENGTH: 54
<212> TYPE: PRT
<213> ORGANISM: Paenibacillus peoriae IBSD35

-continued

```
<400> SEQUENCE: 1

Gly Phe Glu Phe Ala Gly Ala Gly Asn Gly Val Gly Arg Val Asn Ser
1               5                   10                  15

Ala Thr Asp Ala Thr Tyr Gly Leu Gly Val Phe Leu Asp Ala Gly Asp
            20                  25                  30

Asn Asn Leu Ala Lys Asn Ala Glu Ser Thr Gly Tyr Asn Asp Ala Asn
        35                  40                  45

Ala Val Thr Val Thr Lys
    50
```